United States Patent
Nakadozono et al.

(10) Patent No.: US 11,988,622 B2
(45) Date of Patent: May 21, 2024

(54) WATER QUALITY ANALYZER THAT MONITORS PRESSURE AND TEMPERATURE TO ABNORMALITY

(71) Applicant: SHIMADZU CORPORATION, Kyoto (JP)

(72) Inventors: Kenichi Nakadozono, Kyoto (JP); Takeshi Iharada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 421 days.

(21) Appl. No.: 17/414,380

(22) PCT Filed: Sep. 26, 2019

(86) PCT No.: PCT/JP2019/037952
§ 371 (c)(1),
(2) Date: Jun. 16, 2021

(87) PCT Pub. No.: WO2020/129347
PCT Pub. Date: Jun. 25, 2020

(65) Prior Publication Data
US 2022/0050070 A1  Feb. 17, 2022

(30) Foreign Application Priority Data
Dec. 21, 2018 (JP) ................................ 2018-239247

(51) Int. Cl.
*G01N 25/24* (2006.01)
*G01N 33/18* (2006.01)

(52) U.S. Cl.
CPC ............. *G01N 25/24* (2013.01); *G01N 33/18* (2013.01)

(58) Field of Classification Search
CPC .... G01N 25/24; G01N 33/18; G01N 33/1846; G01N 31/12
See application file for complete search history.

(56) References Cited

FOREIGN PATENT DOCUMENTS

| JP | 59-122948 A | 7/1984 | |
|----|---|---|---|
| JP | 2013-185884 A | * 9/2013 | |
| JP | 2013185884 A | * 9/2013 | ............. G01N 31/00 |

(Continued)

OTHER PUBLICATIONS

Office Action dated Mar. 31, 2023 in Chinese Application No. 201980073217.6.

(Continued)

*Primary Examiner* — Eric S. McCall
*Assistant Examiner* — Timothy P Graves
(74) *Attorney, Agent, or Firm* — Sughrue Mion, PLLC

(57) ABSTRACT

A water quality analyzer includes a combustion tube (2) for burning a liquid sample inside, a sample injector (6; 8) that executes sample injection operation into the combustion tube (2), a pressure sensor (28) that detects pressure inside the combustion tube (2), a temperature sensor (38) that detects a temperature of the combustion tube (2), and a determination part (46) configured to determine whether the combustion tube (2) and/or the sample injector (6; 8) is normal or abnormal based on an output of the pressure sensor (28) and an output of the temperature sensor (38) immediately after the sample injection operation by the sample injector (6; 8) is executed.

4 Claims, 2 Drawing Sheets

(56) References Cited

FOREIGN PATENT DOCUMENTS

WO     WO-2010108802 A1 *   9/2010   ......... G01N 33/1846

OTHER PUBLICATIONS

Office Action dated Nov. 18, 2022 in Chinese Application No. 201980073217.6.
Extended European Search Report dated Jul. 11, 2022, issued in European Application No. 19899266.1.
Office Action dated Apr. 19, 2022 issued by the Japanese Patent Office in Japanese Application No. 2020-561164.

* cited by examiner

WATER QUALITY ANALYZER THAT MONITORS PRESSURE AND TEMPERATURE TO ABNORMALITY

TECHNICAL FIELD

The present invention relates to a water quality analyzer.

BACKGROUND ART

As one of water quality analyzers, a combustion oxidation type total organic carbon measuring device (TOC meter) is known (see Patent Document 1). The TOC meter heats a combustion tube in which an oxidation catalyst is arranged to a high temperature (for example, about 680° C.) by an electric furnace, and supplies carrier gas to the combustion tube at a constant flow rate. When a liquid sample is injected into the combustion tube, a carbon component contained in the sample is converted to carbon dioxide by the action of the oxidation catalyst. A detector such as an infrared carbon dioxide detector (NDIR) is connected to the combustion tube, and the carbon dioxide generated in the combustion tube is guided to the detector together with the carrier gas so that the concentration of the carbon dioxide is measured.

PRIOR ART DOCUMENTS

Patent Documents

Patent Document 1: Japanese Patent Laid-open Publication No. 2013-185884
Patent Document 2: Japanese Patent Laid-open Publication No. S59-122948

SUMMARY OF THE INVENTION

Problems to be Solved by the Invention

When the analysis is performed, the value measured by the detector may be zero or close to zero. In a case where such a measured value is obtained, it is difficult for the user to determine whether the measured value is a correct measured value of the sample or due to an abnormality in the device. The abnormalities of the device are considered to include an abnormality of a sample injector that injects the sample into the combustion tube and an abnormality of the combustion tube itself.

Examples of abnormalities of the sample injector include that the sample is not normally injected from the sample injector into the combustion tube due to a defect in sample supply to a sample tank, blockage of a water sampling tube, or the like. In contrast, examples of abnormalities of the combustion tube include that the sample gas is not normally transferred from the combustion tube to the detector due to occurrence of leakage of the carrier gas as the combustion tube is cracked or broken due to deterioration over time and the like, or the pipe is not sufficiently attached to the combustion tube.

Detecting whether or not a sample is normally injected into a combustion tube based on a temperature change or a pressure change in the combustion tube has been proposed (see Patent Documents 1 and 2). However, these methods cannot detect anomalies in the combustion tube.

In order to check whether there is an abnormality in the combustion tube, it is necessary to take the combustion tube out of the electric furnace for checking, which is a time-consuming and labor-intensive task. In order to detect leakage of carrier gas due to an abnormality in the combustion tube, it is possible to take measures such as installing a flow sensor that monitors a carrier gas flow rate downstream of the combustion tube. However, there is a problem that the device cost increases.

The present invention has been made in view of the above problems, and an object of the present invention is to enable detection of the presence or absence of an abnormality in the sample injector and the combustion tube.

Solutions to the Problems

A water quality analyzer includes a combustion tube for burning a liquid sample inside, a sample injector that executes sample injection operation into the combustion tube, a pressure sensor that detects pressure inside the combustion tube, a temperature sensor that detects a temperature of the combustion tube, and a determination part configured to determine whether the combustion tube and/or the sample injector is normal or abnormal based on an output of the pressure sensor and an output of the temperature sensor immediately after execution of the sample injection operation by the sample injector.

When a liquid sample is injected into the combustion tube, the temperature inside the combustion tube decreases due to the heat of vaporization of the liquid sample. Therefore, if a decrease in temperature in the combustion tube is detected, it is possible to detect that the sample is injected into the combustion tube.

Further, when water changes from a liquid state to a gas state, the volume expands up to about 700 times. When a liquid sample is injected into the combustion tube heated to a high temperature, water is instantly vaporized in the combustion tube and the volume expands, and the pressure in the combustion tube increases rapidly. When the pressure in the combustion tube increases, the pressure in the carrier gas supply flow path that is fluidly connected to the combustion tube also increases. Therefore, by monitoring the pressure in the carrier gas supply flow path, it is possible to detect whether or not a liquid sample is injected into the combustion tube.

From the above phenomenon, if both the sample injector and the combustion tube are normal, a temperature fluctuation in the combustion tube and a pressure fluctuation in the combustion tube should be detected immediately after the sample injector executes the sample injection operation. In a case where a sample is not injected into the combustion tube due to an abnormality in the sample injector, no temperature fluctuation in the combustion tube or pressure fluctuation in the combustion tube is detected. In contrast, in a case where there is an abnormality such as a crack in the combustion tube, a temperature fluctuation in the combustion tube is detected immediately after the sample injector executes the sample injection operation. However, no pressure fluctuation in the combustion tube is detected, or, even if there is a pressure fluctuation, a range of the fluctuation is small. Therefore, by monitoring an output of the pressure sensor and an output of the temperature sensor immediately after the sample injection operation by the sample injector is executed, it is possible to detect the presence or absence of an abnormality in the sample injector and the combustion tube.

Effects of the Invention

The water quality analyzer according to the present invention includes a determination part that determines whether the combustion tube and/or the sample injector is normal or abnormal based on an output of the pressure sensor and an output of the temperature sensor immediately after execution of the sample injection operation by the sample injector. Accordingly, it is possible to detect the presence or absence of an abnormality in the sample injector and the combustion tube.

EMBODIMENT OF THE INVENTION

Hereinafter, an embodiment of a water quality analyzer according to the present invention will be described with reference to the drawings.

Figure 1:
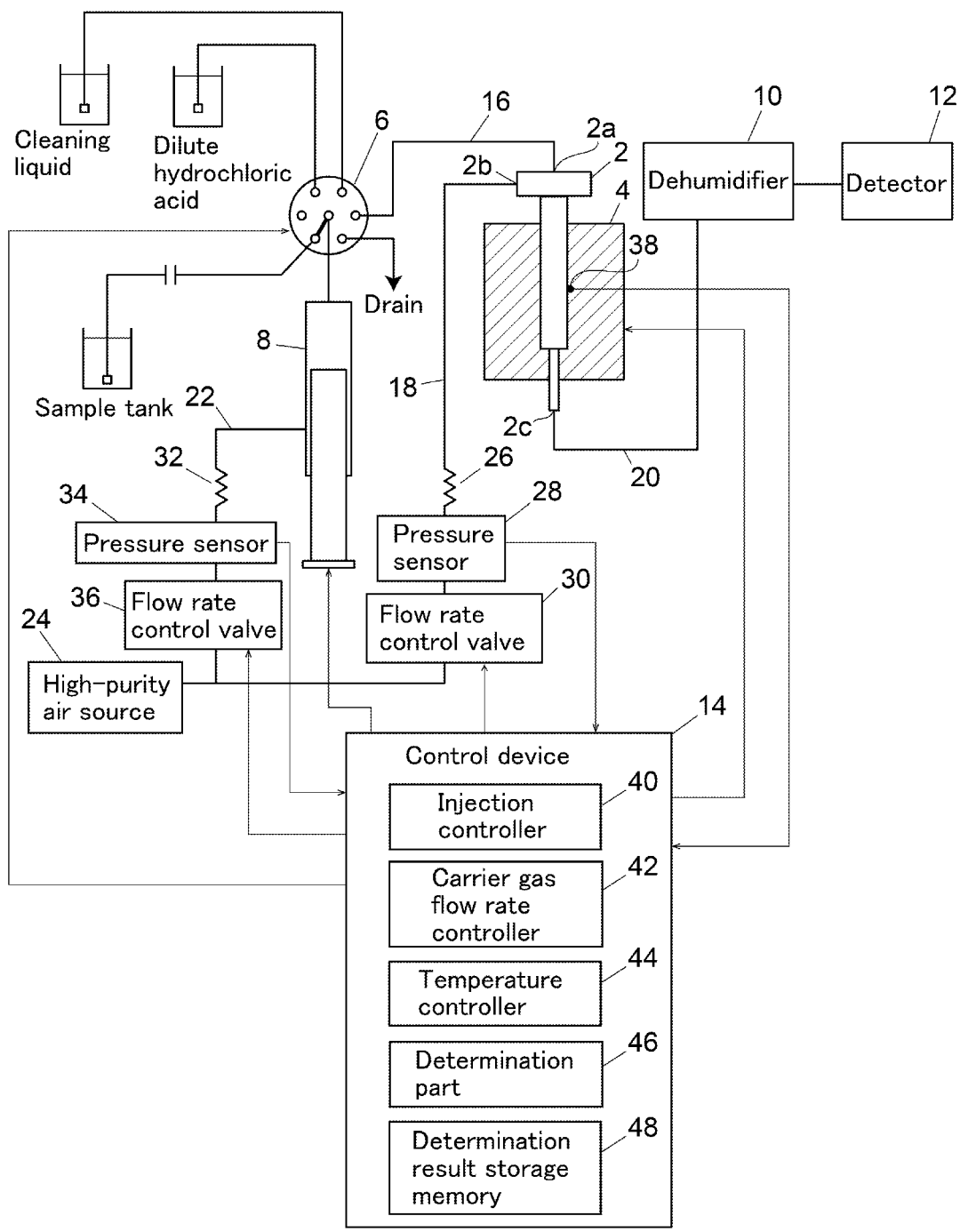
FIG. 1 is a schematic configuration diagram illustrating an embodiment of a water quality analyzer.

FIG. 1 shows a schematic configuration of a combustion oxidation type TOC meter, which is one of water quality analyzers.

The TOC meter of the present embodiment mainly includes a combustion tube 2, an electric furnace 4, a switching valve 6, a syringe pump 8, a dehumidifier, a detector 12, and a control device 14.

The combustion tube 2 is made from, for example, quartz glass, and an oxidation catalyst is arranged inside. The combustion tube 2 is heated by the electric furnace 4 to a high temperature (for example, 680° C.) and burns a liquid sample injected to the inside to generate sample gas. The combustion tube 2 includes a sample injection port 2a for injecting a sample to the inside, a carrier gas introduction port 2b for introducing carrier gas to the inside, and a sample gas outlet 2c for allowing sample gas generated by burning of the sample inside to flow out together with the carrier gas. A sample introduction flow path 16 is connected to the sample injection port 2a of the combustion tube 2, a carrier gas supply flow path 18 is connected to the carrier gas introduction port 2b, and a sample gas flow path 20 is connected to the sample gas outlet 2c. The sample introduction flow path 16 is connected to one selection port of the switching valve 6.

A temperature sensor 38 is attached to the combustion tube 2. The output of the temperature sensor 38 is taken into the control device 14. The control device 14 controls the heating output of the electric furnace 4 so that the temperature of the combustion tube 2 becomes a predetermined temperature based on the temperature detected by the temperature sensor 38.

The switching valve 6 has one central port and a plurality of selection ports. In addition to the sample introduction flow path 16, a flow path leading to a sample tank, a flow path leading to a dilute hydrochloric acid container, a flow path leading to a cleaning liquid container, and a flow path leading to the drain are connected to a plurality of the selection ports of the switching valve 6. A suction/discharge port of the syringe pump 8 is connected to the central port of the switching valve 6, and a connection destination of the suction/discharge port of the syringe pump 8 can be switched by the switching valve 6.

The switching valve 6 and the syringe pump 8 constitute a sample injector for automatically performing injection operation of a sample into the combustion tube 2. The sample injection operation into the combustion tube 2 is operation, in which the syringe pump 8 is connected to the sample tank, a sample in the sample tank is collected in the syringe pump 8, processing, such as addition of acid to the sample or sparging, is performed in the syringe pump 8 if necessary, and then the sample is injected into the combustion tube 2 through the sample injection port 2a.

The carrier gas supply flow path 18 is a flow path for supplying high-purity air from a high-purity air source 24 as carrier gas to the combustion tube 2. A resistance pipe 26, a pressure sensor 28, and a flow rate control valve 30 are provided on the carrier gas supply flow path 18. The pressure sensor 28 is for detecting the pressure in the carrier gas supply flow path 18. An output signal of the pressure sensor 28 is taken into the control device 14. The flow rate control valve 30 is for controlling a flow rate of the carrier gas flowing through the carrier gas supply flow path 18. The opening degree of the flow rate control valve 30 is controlled by the control device 14 based on an output signal of the pressure sensor 28.

The sample gas flow path 20 from the sample gas outlet 2c of the combustion tube 2 is fluidly connected to the detector 12. The detector 12 is for measuring a carbon dioxide concentration in the sample gas generated in the combustion tube 2, and is, for example, NDIR. A dehumidifier 10 is provided on the sample gas flow path 20, and the moisture in the sample gas flowing out from the sample gas outlet 2c of the combustion tube 2 is removed by the dehumidifier 10.

A sparging gas supply flow path 22 is connected to a syringe of the syringe pump 8, so that sparging processing of a sample can be performed with sparging gas in the syringe pump 8. The sparging gas supply flow path 22 is a flow path for supplying high-purity air from the high-purity air source 24 as sparging gas into the syringe of the syringe pump 8. A resistance pipe 32, a pressure sensor 34, and a flow rate control valve 36 are provided on the sparging gas supply flow path 22. The pressure sensor 34 is for detecting the pressure in the sparging gas supply flow path 22. An output signal of the pressure sensor 34 is taken into the control device 14. The flow rate control valve 36 is for controlling a flow rate of the sparging gas flowing through the sparging gas supply flow path 22. The opening degree of the flow rate control valve 36 is controlled by the control device 14 based on an output signal of the pressure sensor 34. Note that the sparging gas supply flow path 22 does not need to be provided.

The control device 14 is for controlling the operation of the switching valve 6, the syringe pump 8, the flow rate control valve 30, and the flow rate control valve 36. The control device 14 is realized by, for example, an electronic circuit including an arithmetic element such as a central processing unit (CPU) and a storage device.

The control device 14 includes an injection controller 40, a carrier gas flow rate controller 42, a temperature controller 44, a determination part 46, and a determination result storage memory 48. The injection controller 40, the carrier gas flow rate controller 42, the temperature controller 44, and the determination part 46 are functions obtained by the arithmetic element executing a program. The determination result storage memory 48 is a function realized by a part of the storage region of the storage device.

The injection controller 40 is configured to control the operation of the sample injector including the switching valve 6 and the syringe pump 8 to execute the injection operation of a sample into the combustion tube 2. The injection controller 40 transmits a necessary signal to a driver that drives the switching valve 6 and the syringe pump 8 when the user inputs a sample injection instruction to the control device 14 or when a preset sample injection time (for example, a time at a fixed time interval from the start of measurement) is reached, so that the sample injection operation into the combustion tube 2 is executed.

The carrier gas flow rate controller 42 is configured to control the opening degree of the flow rate control valve 30 so that a flow rate of the carrier gas flowing through the carrier gas supply flow path 18 becomes a preset flow rate based on an output signal of the pressure sensor 28.

The temperature controller 44 is configured to control the heating output of the electric furnace 4 so that the temperature of the combustion tube 2 becomes a predetermined temperature based on an output signal of the temperature sensor 38.

The determination part 46 is configured to detect the presence or absence of an output signal of the pressure sensor 28 and an output signal of the temperature sensor 38 immediately after the sample injection operation by the sample injector is executed, and, based on a result of the detection, determine whether each of the sample injector and the combustion tube 2 is normal or abnormal.

The determination result storage memory 48 stores a determination result by the determination part 46. A determination result stored in the determination result storage memory 48 can be displayed on a display device (not shown) together with a measurement result obtained by the detector 12, for example. In this manner, in a case where there is an abnormality in a measurement result, it can be verified after the fact whether or not the abnormality is due to an abnormality in the sample injection. Further, the injection controller 40 may be configured to stop the subsequent sample injection operation when the combustion tube 2 is determined to be abnormal as a result of the determination by the determination part 46. This prevents unnecessary analysis of a sample from being performed.

In the present embodiment, the flow rate of the carrier gas supplied to the combustion tube 2 through the carrier gas supply flow path 18 is electronically controlled by using the pressure sensor 28 and the flow rate control valve 30. Then, the determination part 46 of the control device 14 determines whether each of the sample injector and the combustion tube 2 is normal or abnormal by using the pressure sensor 28 originally provided for controlling the carrier gas flow rate and the temperature sensor 38 originally provided for the temperature control of the combustion tube 2. That is, in the present embodiment, a function of determining whether each of the sample injector and the combustion tube 2 is normal or abnormal is realized only by changing a software configuration of the control device 14 without changing an existing device configuration.

Figure 2:
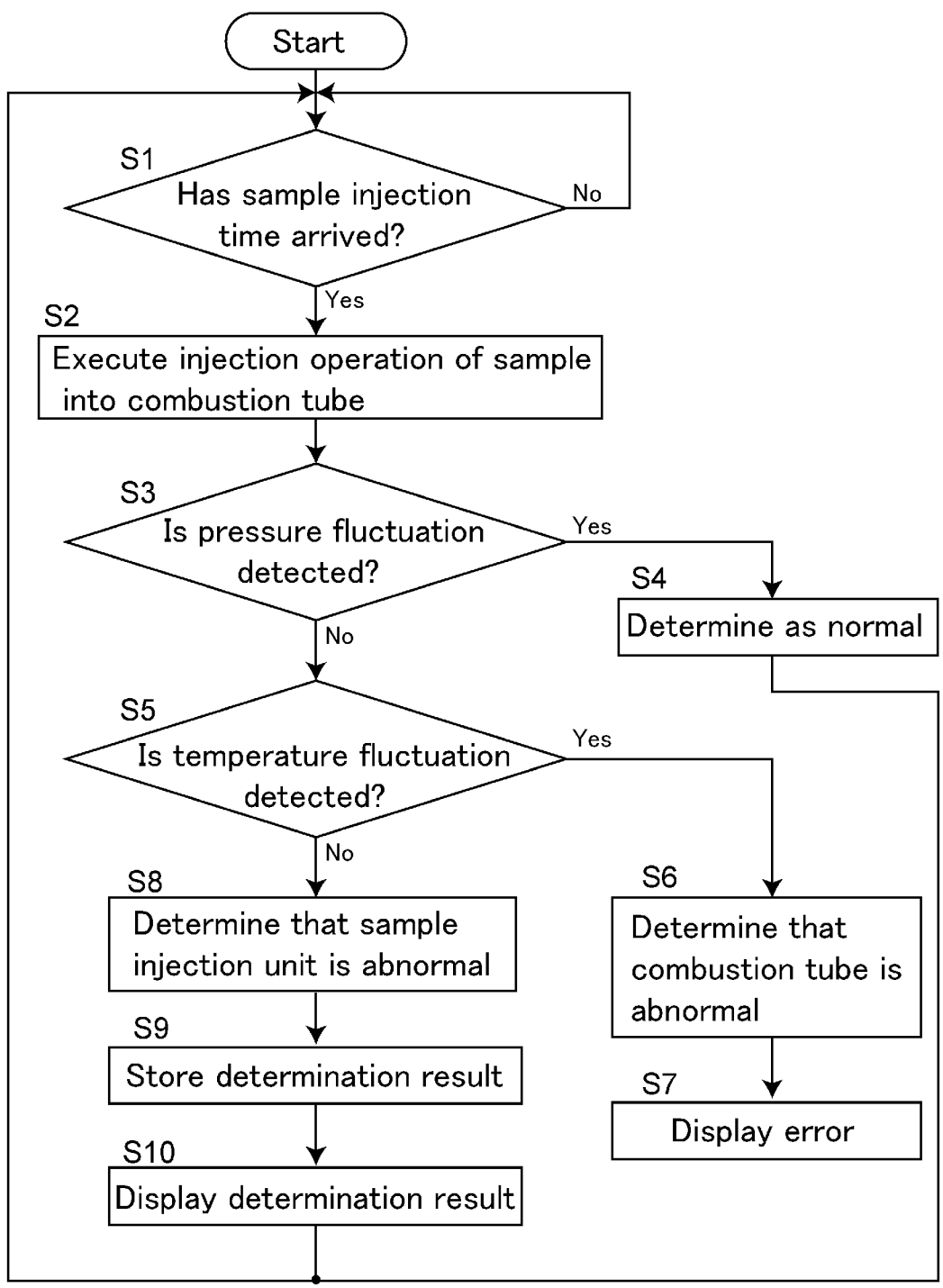
FIG. 2 is a flowchart showing an example of a determination operation in the embodiment.

The determination operation by the determination part 46 will be described with reference to the flowchart of FIG. 2 together with FIG. 1. Here, an example in which the injection operation of a sample into the combustion tube 2 is automatically executed at a preset sample injection time will be described.

When the preset sample injection time arrives, the injection controller 40 transmits a signal to the driver driving the switching valve 6 and the syringe pump 8 to execute the sample injection operation into the combustion tube 2 (Steps S1 and S2). The determination part 46 monitors output signals of the pressure sensor 28 and the temperature sensor 38 immediately after the sample injection operation is executed, and detects the presence or absence of a fluctuation in these output signals. The presence or absence of a fluctuation in an output signal of the pressure sensor 28 is determined by whether or not the output signal of the pressure sensor 28 exceeds a predetermined threshold value (first threshold value). The presence or absence of a fluctuation in an output signal of the temperature sensor 38 is determined by whether or not the output signal of the temperature sensor 38 is below a predetermined threshold value (second threshold value).

In a case where a pressure fluctuation in the combustion tube 2 is detected immediately after the sample injection operation is executed (Step S3), it can be determined that the sample is normally injected into the combustion tube 2, and the pressure in the combustion tube 2 is temporarily increased. Therefore, when the pressure fluctuation in the combustion tube 2 is detected, the determination part 46 determines that both the sample injector and the combustion tube 2 are normal (Step S4).

In contrast, in a case where no pressure fluctuation in the combustion tube 2 is detected after the sample injection operation is executed, it can be determined that the sample is not normally injected into the combustion tube 2, or the combustion tube 2 has a problem such as a crack. In view of the above, in a case where no pressure fluctuation in the combustion tube 2 is detected after the sample injection operation is executed, the determination part 46 detects the presence or absence of a fluctuation in an output signal of the temperature sensor 38 (Step S5), and determines whether the sample injector is normal while there is an abnormality in the combustion tube 2 if a fluctuation in the output signal of the temperature sensor 38 is detected (Step S6) or there is an abnormality in the sample injector if no fluctuation in the output signal of the temperature sensor 38 is detected, either (Step S8).

In a case where there is an abnormality in the combustion tube 2 (Step S6), leakage of the carrier gas occurs and the analysis cannot be performed normally. Therefore, an error is displayed on a predetermined display unit and the subsequent analysis operation is suspended. In contrast, in a case where there is an abnormality in the sample injector (Step S8), the determination result is stored in the determination result storage memory 48 (Step S9), and the determination result is displayed on a predetermined display unit (Step S10). Note that, even in a case where the combustion tube 2 is determined to be abnormal, the determination result may be configured to be stored in the determination result storage memory 48.

The embodiment described above is merely an example of embodiments of the water quality analyzer according to the present invention. An embodiment of the water quality analyzer according to the present invention is as described below.

The embodiment of the water quality analyzer according to the present invention includes the combustion tube (2) for burning a liquid sample inside, the sample injector (6; 8) that executes sample injection operation into the combustion tube (2), the pressure sensor (28) that detects pressure inside the combustion tube (2), the temperature sensor (38) that detects a temperature of the combustion tube (2), and the determination part (46) configured to determine whether the combustion tube (2) and/or the sample injector (6; 8) is normal or abnormal based on an output of the pressure sensor (28) and an output of the temperature sensor (38) immediately after execution of the sample injection operation by the sample injector (6; 8).

In a first aspect of the embodiment of the water quality analyzer according to the present invention, the determination part (46) is configured to detect the presence or absence of a fluctuation in an output of the pressure sensor (28) and the presence or absence of a fluctuation in an output of the temperature sensor (38) immediately after execution of the sample injection operation by the sample injector (6; 8), and, based on a result of the detection, determine whether the combustion tube (2) and/or the sample injector (6; 8) is normal or abnormal.

In the first aspect, the determination part (46) can be configured to determine that the combustion tube (2) and the sample injector (6; 8) are normal when detecting a fluctuation in the output of the pressure sensor (28), determine that the combustion tube (2) is abnormal and the sample injector (6; 8) is normal when detecting only a fluctuation in the output of the temperature sensor (38), and to determine that the sample injector (6; 8) is abnormal when not detecting any fluctuation in either the output of the pressure sensor (28) or the output of the temperature sensor (38).

Further, in the first aspect, the determination part (46) can be configured to detect a fluctuation in the output of the pressure sensor (28) when the output of the pressure sensor (28) exceeds a preset first threshold value, and to detect a fluctuation in the output of the temperature sensor (38) when the output of the temperature sensor (38) is below a preset second threshold value.

A second aspect of the embodiment of the water quality analyzer according to the present invention further includes a determination result storage memory (48) that stores a determination result by the determination part (46). By the above aspect, in a case where there is an abnormality in a measurement result, it can be verified after the fact whether or not the abnormality is due to an abnormality in the sample injector (6; 8) or the combustion tube (2).

A third aspect of the embodiment of the water quality analyzer according to the present invention further includes a carrier gas supply flow path (18) that is fluidly connected to the combustion tube (2) for supplying carrier gas into the combustion tube (2), in which the pressure sensor (28) is provided on the carrier gas supply flow path (18). By the above aspect, since an output signal of the pressure sensor (28) provided for controlling a flow rate of the carrier gas supplied to the combustion tube (2) is used for the determination by the determination part (46), the function of the determination part 46 can be realized by using an existing device configuration, and an increase in the device cost can be suppressed.

DESCRIPTION OF REFERENCE SIGNS

2: Combustion tube
2*a*: Sample injection port
2*b*: Carrier gas introduction port
2*c*: Sample gas outlet
4: Electric furnace
6: Switching valve
8: Syringe pump
10: Dehumidifier
12: Detector
14: Control device
16: Sample introduction flow path
18: Carrier gas supply flow path
20: Sample gas flow path
22: Sparging gas supply flow path
24: High-purity air source
26, 32: Resistance pipe
28, 32: Pressure sensor
30, 36: Flow rate control valve
38: Temperature sensor
40: Injection controller
42: Carrier gas flow rate controller
44: Temperature controller
46: Determination part
48: Determination result storage memory

The invention claimed is:

1. A water quality analyzer comprising:
a combustion tube for burning a liquid sample inside;
a sample injector that executes sample injection operation into the combustion tube;
a pressure sensor that detects pressure inside the combustion tube;
a temperature sensor that detects a temperature of the combustion tube; and
a determination part configured to determine whether the combustion tube and/or the sample injector is normal or abnormal based on an output of the pressure sensor and an output of the temperature sensor immediately after execution of the sample injection operation by the sample injector, wherein
the determination part is configured to detect presence or absence of a fluctuation in an output of the pressure sensor and presence or absence of a fluctuation in an output of the temperature sensor immediately after execution of the sample injection operation by the sample injector, and, based on a result of the detection, determine whether the combustion tube and/or the sample injector is normal or abnormal, and
the determination part is configured to determine that the combustion tube and the sample injector are normal when detecting a fluctuation in the output of the pressure sensor, to determine that the combustion tube is abnormal and the sample injector is normal when detecting only a fluctuation in the output of the temperature sensor, and to determine that the sample injector is abnormal when not detecting any fluctuation in either the output of the pressure sensor or the output of the temperature sensor.

2. The water quality analyzer according to claim 1, wherein the determination part is configured to detect a fluctuation in the output of the pressure sensor when the output of the pressure sensor exceeds a preset first threshold value, and to detect a fluctuation in the output of the temperature sensor when the output of the temperature sensor is below a preset second threshold value.

3. The water quality analyzer according to claim 1, further comprising a determination result storage memory that stores a determination result by the determination part.

4. The water quality analyzer according to claim 1, further comprising a carrier gas supply flow path that is fluidly connected to the combustion tube for supplying carrier gas into the combustion tube,
wherein the pressure sensor is provided on the carrier gas supply flow path.

* * * * *